United States Patent [19]

Woodrum

[11] Patent Number: 4,959,305
[45] Date of Patent: Sep. 25, 1990

[54] REVERSIBLE IMMOBILIZATION OF ASSAY REAGENTS IN A MULTIZONE TEST DEVICE

[75] Inventor: David L. Woodrum, Rancho Palos Verdes, Calif.

[73] Assignee: Miles Inc., Elkhart, Ind.

[21] Appl. No.: 265,303

[22] Filed: Oct. 31, 1988

Related U.S. Application Data

[63] Continuation of Ser. No. 875,464, Jun. 18, 1986, abandoned.

[51] Int. Cl.$^5$ ............... G01N 31/22; G01N 33/53
[52] U.S. Cl. ............................ 435/7; 422/56; 422/57; 422/58; 436/170; 435/805
[58] Field of Search ........................... 422/56–58; 435/7, 805; 436/170

[56] References Cited

U.S. PATENT DOCUMENTS

| Re. 30,267 | 5/1981 | Bruschi | 436/170 |
| 4,088,538 | 5/1978 | Schneider | 435/94 |
| 4,120,945 | 10/1978 | Gutcho et al. | 422/57 X |
| 4,144,306 | 3/1979 | Figueras | 422/56 |
| 4,258,001 | 3/1981 | Pierce et al. | 436/170 X |
| 4,277,560 | 7/1981 | Gray et al. | 422/81 X |

FOREIGN PATENT DOCUMENTS 0253581 1/1988 European Pat. Off. .
2729268 2/1978 Fed. Rep. of Germany .
3445816 6/1986 Fed. Rep. of Germany .
8604683 8/1986 PCT Int'l Appl. .

OTHER PUBLICATIONS

Chem. Abstract 89:38969y.

Primary Examiner—Robert J. Warden
Attorney, Agent, or Firm—Andrew L. Klawitter; Daniel W. Collins

[57] ABSTRACT

A multizone test device for the determination of analyte in a liquid test medium. The test device preferably comprises multilayers including a first layer comprising a solid, porous matrix incorporated with a reversibly immobilized first reagent and a second layer comprising a solid, porous matrix incorporated with a second reagent which interacts with the first reagent and analyte from the liquid test medium to provide a detectable signal. A reversible binding interaction between the first reagent and the matrix of the first layer prevents the first reagent from prematurely migrating into the second layer during manufacture of the device and prior to application of the liquid test medium to the test device. The reversible binding interaction is sufficiently disruptable by contact of the first layer with the liquid test medium to release and thereby render diffusible an analytically effective amount of the first reagent within the test device.

20 Claims, 2 Drawing Sheets

REVERSIBLE IMMOBILIZATION OF ASSAY REAGENTS IN A MULTIZONE TEST DEVICE

This is a continuation, of application Ser. No. 875,464, filed June 18, 1986, now abandoned.

BACKGROUND OF THE INVENTION

1. Field of the Invention

The present invention relates to analytical test devices which are useful for the determination of an analyte in a liquid test medium. In particular, the present invention relates to multizone test devices incorporated with two or more interactive or incompatible reagents, particularly immunoassay reagents, which provide a detectable signal upon contact with analyte from the liquid test medium.

2. Description of the Prior Art

One of the problems encountered in the manufacture of test devices comprising one or more reagent zones or layers incorporated with assay reagents is the premature interaction or migration of such reagents, either during the manufacturing process or at a time prior to application of a liquid test sample to such device. Typically, such premature interaction or migration occurs where the casting of such zones or layers involves, for example, materials such as paper, gelatin or agarose which have been hydrated in order to incorporate the various assay reagents therein, or to facilitate the formation of a multilayer test device. In particular, such premature interaction or migration of reagents occurs where a single zone or layer containing interactive assay reagents is cast in a hydrated state, as well as where two or more of such zones or layers are simultaneously cast, or where subsequent hydrated zones or layers are cast over a previously dried or gelled zone or layer. Accordingly, the hydrated states of the zones or layers permits the assay reagents to freely diffuse within or migrate between such zones or layers and prematurely interact therein during the casting and/or drying process, thereby affecting the performance of the device, and in some cases rendering the device essentially inoperative as a result of such interaction.

It is therefore desirable to immobilize, segregate or otherwise prevent the premature migration and subsequent interaction of assay reagents within the various zones or layers of an analytical test element. Variations of such analytical test elements are known in the art and described by, for example, U.S. Pat. Nos. 4,333,733 and 4,356,149. The continuous release of a reagent in an analytical element to reduce assay interference is described by U.S. Pat. No. 4,333,733 wherein the analytical element comprises a reaction zone, to which a liquid test sample is applied, and a reagent zone incorporated with a chromogenic indicator. The reagent zone is impermeable to analyte and protein interferants whereby upon application of the test sample, the liquid portion thereof permeates the reagent zone causing the indicator to be released into the reaction zone. Multilayer chemical analytical materials for the detection of urea are described by U.S. Pat. No. 4,356,149 wherein a reagent layer comprising a hydrophilic binder is incorporated with hydrophobic particles containing an assay reagent therein. The particles are water-impermeable and permeable only to gaseous reaction products, e.g., ammonia, wherein the assay reagent directly, or indirectly, reacts with the gaseous reaction product to produce a change in color.

It is also known in the art to provide multizone, or multilayer, test devices which have various immobilized reagents incorporated therein. Such immobilized reagents are generally employed in such elements or test devices to inherently separate bound and free species formed by, for example, an antigen-antibody reaction.

For example, such multilayer immunoassay analytical elements are described by European Patent Publication No. 97,952 and German Publication No. DE-OS 3329728 where an immobilized form of a binding partner, such as an immobilized antibody to an antigen, and an antigen labeled with a detectable substance are incorporated therein. Upon the application of a liquid test medium to such device, antigen from the test medium competes with labeled antigen incorporated into the device for binding to the immobilized antibody. Separation of the bound species from the free species occurs upon migration of the free species of the labeled antigen away from the immobilized zone.

Similarly, European Patent Publication Nos. 51,183 and 66,648 disclose such devices where the determination or antigen or antibody in a liquid test medium is dependent upon the competitive binding of the antigen (or antibody) with a labeled form of the antigen (or antibody) for an immobilized form of a binding partner thereof, such as immobilized antibody (or antigen).

Another of such devices is described in U.S. Pat. No. 4,446,232 which is based on the principle of competition between bound and free species of analyte for a fixed number of recognition sites on an enzyme-labeled antibody. The determination of analyte in a test sample depends upon the binding of the analyte to enzyme-labeled antibodies in one zone of the device and which then pass into another zone of the device where the enzyme activity of the enzyme-linked antibodies bound to analyte is detected. One of the zones further includes bound and immobilized analyte which competes with analyte from the test sample for binding to the enzyme-labeled antibodies and which bind and immobilize any of the enzyme-labeled antibodies which do not become bound to analyte from the test sample.

Analytical elements and test devices are also known in the art which employ immobilizing agents within a zone or zones of such devices in order to localize reaction products resulting from various specific binding assay reactions within such device.

For example, European Patent Publication Nos. 51,183 and 66, 648 suggest layers for collection of the detectable reaction product comprising hydrophilic high molecular weight substances. EP No. 66,648 further suggests the incorporation of mordanting agents in the detection layer which have a strong interaction with the detectable reaction product in order to collect the detectable reaction product therein. Such mordanting agents include cationic polymers, anionic polymers and quaternary salts.

Similarly, U.S. Pat. Nos. 4,144,306 and 4,042,335 disclose multilayer analytical elements which include a registration layer incorporated with a mordant for a detectable species in order to collect the detectable species therein and thereby prevent diffusion or migration of the detectable species out of the registration layer.

A variation of such devices is disclosed by U.S. Pat. No. 4,459,358 which describes a multilayer element comprising a spreading layer, a reaction layer incorporated with a diffusible labeled antibody, and a registration layer incorporated with materials adapted to non-specifically bind, immobilize or "mordant" antibodies, such as latex particles. Upon application of a liquid test medium to the device, analyte from the test medium associates with the labeled antibody in the reaction layer and immunoprecipitates therein. Any of the labeled antibody which does not become bound to the analyte diffuses into the registration layer where it is immobilized by the mordant incorporated therein.

However, such analytical elements and test devices are directed to the permanent immobilization of reagents which do not participate in the initial assay reactions necessary for the detection of an analyte in a liquid test medium. Although the immobilization of such reagents provides means for preventing the further migration of reaction products formed within a test device, the problem of premature migration and interaction of assay reagents necessary for the formation of reaction products which can be correlated to the amount of an analyte in a liquid test medium nevertheless remains unsolved.

Accordingly, it is an object of the present invention to provide in an analytical test device assay reagents which participate in assay reactions necessary for the determination of analyte from a liquid test medium wherein the reagents are prevented from prematurely migrating and/or interacting during manufacture and prior to application of the liquid test medium to such test device.

Another object of the present invention is to provide for the essentially instantaneous release of reversibly immobilized assay reagents in an analytical test device upon application of a liquid test medium to such test device.

Further, it is an object of the present invention to permit the simultaneous incorporation of otherwise diffusible and interactive assay reagents in a test device during the manufacturing process thereof.

SUMMARY OF THE INVENTION

The present invention provides a multizone test device incorporated with two or more interactive assay reagents which participate in assay reactions necessary for the determination of analyte in a liquid test medium and which are reversibly immobilized within the test device to prevent the premature migration and subsequent interaction thereof prior to application of the liquid test medium to the test device. The present invention is particularly useful during the manufacture and storage of a multizone test device whereby the assay reagents would otherwise be solubilized and prematurely interact with each other during periods of hydration and result in a less useful or essentially inoperative test device.

The test device comprises, in fluid flow contact, a reagent zone comprising a solid, porous matrix incorporated with a reversibly immobilized first reagent and a reaction zone comprising a solid porous matrix incorporated with a second reagent which is capable of interacting with the first reagent. The first reagent is reversibly immobilized within the reagent zone by a reversible binding interaction which exists between the first reagent and the reagent zone matrix, such as between the first reagent and an insolubilized form of a binding substance incorporated into the reagent zone matrix, wherein the first reagent is immobilized and prevented from migrating out of the reagent zone and into the reaction zone prior to application of the liquid test medium thereto. The reversible binding interaction is sufficiently disruptable by contact of the reagent zone with a liquid test medium which specifically interacts with the first reagent and the reagent zone matrix to disrupt the reversible binding interaction therebetween to release and render diffusible an analytically effective amount of the first reagent therein. The first reagent is then permitted to freely diffuse and migrate into the reaction zone to interact with the second reagent incorporated therein to provide the detectable signal which can be correlated to the amount of analyte in the liquid test medium.

The first reagent and the matrix of the reagent zone are selected to comprise binding compositions which possess a stable, specific binding interaction therebetween which is sufficiently disruptable and reversible only by a predetermined liquid test medium having specific interactive properties for the first reagent and/or the matrix to disrupt the binding interaction therebetween. Such specific interactive binding properties between the first reagent and the matrix prevents the non-specific disruption of the binding interaction by, for example, the solvent employed during the formation of the various layers, or hydration of the test device during periods of storage, prior to application of the appropriate liquid test sample having specific disrupting properties for the binding interaction. The reversible binding interaction will therefor depend upon the selected compositions of the first reagent and the matrix and will include reversible binding interactions such as ionic binding interactions, reversible covalent binding interactions, hydrophobic binding interactions, and reversible biochemical binding interactions.

DESCRIPTION OF THE PREFERRED EMBODIMENTS

Figure 1:
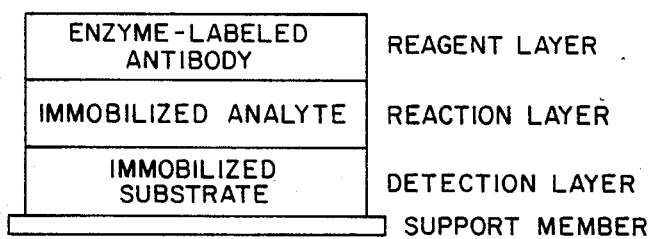
FIG. 1 is a sectional view of a multilayer test device incorporated with reversibly immobilized assay reagents according to the present invention for performing an immunoassay involving an enzyme-labeled antibody as one of the assay reagents.

According to the present invention, the premature migration and subsequent interaction of assay reagents in a zoned or layered analytical test device, prior to application of a liquid test sample thereto, is prevented as a result of the reversible immobilization of one or more assay reagents within one or more zones or layers of such device. The present invention is particularly advantageous over the manufacturing processes of multizone or multilayer test devices according to methods known in the art. According to such known methods, the various zones or layers are either simultaneously or sequentially formed in a hydrated or otherwise fluid state wherein the migration of assay reagents incorporated therein is greatly enhanced, particularly during the manufacturing process. As will be described in greater detail hereinafter, assay reagents which are reversibly immobilized in a multizone or multilayer test device according to the present invention remain nondiffusible and are thereby prevented from prematurely migrating during such manufacturing processes, as well as during periods of storage of such devices, until the assay reagents are brought into direct fluid contact with an appropriate liquid test sample. Upon contact with the sample, the reversibly immobilized reagents are released and rendered diffusible and thereby permitted to freely migrate within such device.

In order to simplify the disclosure hereinafter, the test device described in context of the present invention will now be described principally as comprising a layered structure, although it will be understood that other types of zones can accomplish the same result. In particular, the test device in accordance with the present invention comprises at least two layers, such as a reagent layer and a reaction layer, and as will be described in greater detail hereinafter, can further include a detection layer. The various layers comprise a solid, porous matrix and are in fluid contact with one another whereby the layers of the test device which are associated with each other permit the diffusion of a fluid into and between these layers. Such fluid contact permits the migration of analyte and test reagents from a fluid sample between the layers of the device and is preferably uniform along the contact interface between the fluid contacting layers. Accordingly, upon application of the liquid test sample to the reagent layer, the liquid test sample permeates and diffuses into and through the reagent layer into the reaction layer, and, where a detection layer is provided, into the detection layer.

According to the present invention, the reagent layer is incorporated with a reversibly immobilized first reagent having a reversible interactive binding property for the matrix of the reagent layer, and the reaction layer is incorporated with a second reagent which is capable of interacting with the first reagent to provide a detectable signal. It is to be appreciated that the reversible immobilization of reagents according to the present invention is not to be limited to the reversible immobilization of only the first reagent, or only within the matrix of the reagent layer, but is intended to encompass the reversible immobilization of the second reagent or other interactive assay reagents in additional layers as well. Accordingly, the reversible immobilization of the first reagent will now be described with the reversible immobilization of other interactive assay reagents in various other layers as being intended.

The reversible interactive binding property between the first reagent and the reagent layer matrix is a binding interaction which depends upon the particular composition of the matrix of the reagent layer and/or the first reagent wherein the binding interaction therebetween is sufficiently disruptable upon contact of the matrix with a specific liquid test sample. It is to be understood that preferably the rate of release of a reversibly immobilized assay reagent according to the present invention is essentially instantaneous upon contact with an appropriate liquid test sample. It is intended that such instantaneous release of assay reagents provide a rapid mechanism for the release of a sufficient amount of such reversibly immobilized assay reagents to permit the necessary assay interaction to begin within seconds of application of the test sample.

Accordingly, upon application of the liquid test sample to the device and subsequent disruption of the binding interaction between the first reagent and the matrix, the first reagent is released in an analytically effective amount and rendered diffusible within the reagent layer and thereby free to migrate into the reaction layer. Any of the first reagent which migrates into the reaction layer is then permitted to interact with the second reagent incorporated therein to provide a detectable signal which can be correlated to the amount of analyte in the liquid test sample. For example, where the nature of the binding interaction between the first reagent and the matrix is weakly ionic, the binding interaction therebetween is disruptable by a liquid test sample having a relatively low salt concentration, such as whole blood or serum. It is therefore essential to the present invention that the composition of the matrix and the first reagent be selected to comprise binding compositions which possess a stable binding interaction therebetween which is sufficiently disruptable and reversible only by a predetermined liquid test sample having the necessary, specific interactive disrupting properties to disrupt the binding interaction between such first reagent and matrix. It is to be appreciated that selection of an appropriate solvent for use during the formation of the reagent layer according to the present invention, as well as for the formation of subsequent layers, is also essential to the present invention. In particular, such solvent must be inert with respect to the reversible binding interaction between the first reagent and the reagent layer matrix. Accordingly, the first reagent will remain bound to the reagent layer matrix in the presence of the solvent wherein the binding interaction remains stable and is not capable of being disrupted by the solvent as a result of the inert nature thereof.

The present invention is particularly advantageous over known prior art methods and manufacturing processes of multilayer test devices. For example, according to such methods known in the art, the manufacture of a multilayer test device typically involves the steps of (a) incorporating a first or overlaying zone with some of the assay reagents of a reaction system, (b) incorporating a second or underlaying zone with the remainder of assay reagents necessary to interact with assay reagents from step (a), (c) drying the individual layers, and (d) fixing the layers into a laminar relationship with one another. Other methods include forming individual layers with a Meyer rod or cascade coater and laminating such layers with spacing layers therebetween, and which similarly require drying the layers prior to lamination. According to such methods, it is necessary to dry each of the individual layers prior to the lamination thereof in order to prevent the migration of, for example, reagents from the first zone into the second zone, or vice versa, as a result of the fluidity between the zones if otherwise laminated when wet.

Accordingly, the selection of such compatible compositions having the desired interactive properties according to the present invention permits the simultaneous incorporation of assay reagents in the various layers as described above, as well as the simultaneous assembly of such layers without the need to dry each of the layers prior to the assembly or lamination thereof. Such interactive properties thus prevent the non-specific disruption of the binding interactions between the assay reagents and matrices by, for example, the solvent employed during the formation of such layers as described above, or during periods of storage of the completed device, prior to application of the appropriate liquid test sample having specific disrupting properties for the binding interaction therebetween.

Reversible Binding Systems

According to the present invention, a variety of binding interactions may be employed to reversibly immobilize assay reagents within the various layers of a multilayer test device. As described above, such binding interactions depend upon the interactive properties of and between (a) the assay reagents and (b) the matrix comprising the incorporating layer of the reversibly immobilized assay reagents, and (c) the disruptive properties of the liquid test sample necessary to disrupt the particular reversible binding interaction between the assay reagents and the matrix to thereby release and render diffusible the assay reagents in an analytically effective amount within the device. Such disruptable binding interactions are known in the art and include, but are not intended to be limited to: ionic binding interactions; reversible covalent binding interactions; hydrophobic binding interactions; reversible biochemical binding affinities; and the like.

(a) Interactive Assay Reagents

The assay reagents which can be reversibly immobilized within a test device according to the present invention may be (i) any assay reagent which is capable of interacting with the analyte from the liquid test sample to generate a detectable signal having an intensity which is dependent upon the amount of analyte present, or (ii) any assay reagent which is necessary to participate in an assay reaction or otherwise interact with the analyte and/or other assay reagents to generate such detectable signal. Accordingly, depending upon the signal generated and the signal detection system incorporated into a particular device, upon contact with the liquid test sample and subsequent disruption of the reversible binding interaction between the reversibly immobilized assay reagent and the matrix as heretofore described, the assay reagent is released and rendered diffusible and thereby permitted to interact with the analyte and/or other assay reagents to generate the detectable signal.

In general, such signal-generating interaction between the analyte under determination and one or more assay reagents, or between, for example, a first reagent and a second reagent, can be a chemical interaction or activity, catalytic activity as in the formation of an enzyme-substrate complex, or any other known form of chemical or physical interaction that can release, produce, or otherwise provide a detectable signal which can be correlated to the presence and/or concentration of the analyte under determination.

The present invention is particularly useful in carrying out immunoassays. In such assays, the reversibly immobilized first reagent as described above preferably comprises a labeled form of the analyte or binding analog thereof, or a labeled form of a binding partner of the analyte, labeled with a detectable chemical group having a detectable physical, chemical or interactive property. Such detectable chemical groups have been well developed in the field of assay reaction systems and, in general, most any label in such methods can be applied to the present invention.

In particular, such chemical groups having detectable physical properties are those groups which are detected on the basis of their own physical properties which do not require a chemical reaction or interaction with another chemical or substance to provide a detectable signal. Such groups principally include fluorescers such as umbelliferone, fluorescein, resorufin, various rhodamines, dansyl derivatives and aminonaphthalenesulfonic acid, (see Clin. Chem. (1979) 25:353); phosphorescent molecules such as pyrene, 4-nitrobiphenyl, benzaldehyde, benzophenone or the trivalent metal chelates of dibenzoylmethane (e.g., $Al^{+3}$, $Sc^{+3}$, $T^{+3}$); chromophores such as paraor ortho-nitrophenol, phenolphthalein, napthol AS, para-nitroanilide and thymolphthalein; radioisotopes such as $^3H$, $^{35}S$, $^{32}P$, $^{125}I$ and $^{14}C$; spin labels including nitroxide radicals such as DOXYL, PROXYL and TEMPO derivatives; or electroactive moieties such as protons, fluoride, oxygen, ammonia and hydrogen peroxide.

Chemical groups having detectable chemical properties are those groups which are detected on the basis of their own chemical reactivity or interaction with another substance to provide a detectable signal. Such chemical groups having detectable chemical properties do not generate a detectable product or otherwise provide a detectable signal prior to interacting with another reagent and include enzymatically active groups such as enzymes (see Clin. Chem. (1976) 22:1232, U.S. Reissue Pat. No. 31,006, and U.K. Pat. No. 2,019,308), enzyme substrates (see British Pat. Spec. No. 1,548,741), coenzymes (see U.S. Pat. Nos. 4,230,797 and 4,238,565), enzyme inhibitors and activators, chemiluminescent species, chemical catalysts, metal catalysts, members of enzyme channeling, fluorophor-quencher, or energy transfer pairs (see U.S. Pat. Nos. 3,996,345; 4,174,384; 4,199,559, and 4,233,402), and specifically bindable ligands such as biotin or a hapten. For example, a cofactor-labeled species can be detected by adding the enzyme for which the label is a cofactor and a substrate or substrates for the enzyme. Also, a hapten or other specifically bindable ligand (e.g., biotin) labeled species can be detected by adding an antibody to the hapten or a protein (e.g., avidin) which binds the ligand tagged or labeled with a detectable molecule. Such detectable molecule can be some molecule with a measurable physical property (e.g., fluorescence or absorbance).

It is to be appreciated that according to the present invention, the reversible binding interaction between, for example, the first reagent and the matrix of the incorporating layer can be (i) between the analyte or analog thereof, or binding partner of the analyte, and the matrix, or (ii) between the particular label and the matrix. In addition to the binding interactions as set forth in (i) and (ii) above, a "generic" reversible binding interaction can be provided between the matrix and a linking group through which the label is coupled to the analyte or analog thereof, or to the binding partner of the analyte, or between the matrix and some other derivative moiety that has been chemically added to the analyte, analog, or binding partner. This is accomplished by incorporating a generic moiety into the linking or other derivative group which interacts with the matrix of the incorporating layer to reversibly immobilize the first reagent therein. Reliance upon the reversible interactive binding properties of such linking or derivative group, rather than the reversible binding properties of the label and/or analyte or analog thereof, or binding partner of the analyte of the first reagent, is particularly preferred because alteration of the basic chemistry of the system is not required, wherein a number of first reagent compositions could therefore be synthesized employing a standardized or generic linking or derivative group, all of which would be compatible with a common matrix composition. For example, a dye label such as rhodamine or sulforhodamine could be coupled to an analyte through a piperazine group wherein in each case, the reversible immobilization of such reagent is the result of the interaction between the piperazine group and a common, compatible matrix composition, such as carboxymethyl cellulose.

Other generic moieties include α-D-mannopyranosyl, α-D-glucopyranosyl, or sterically related groups which can be incorporated into the linking group or derivatization group of a labeled reagent and reversibly immobilized to a matrix composition comprising, for example, concanavalin-A and cross-linked agarose wherein such binding interaction is disrupted by a liquid test sample containing α-methyl mannoside. Similarly, N-acetylglucosamine, and disaccharide and trisaccharide derivatives thereof, can be incorporated into the linking group or derivatization group of a labeled reagent and reversibly immobilized to a matrix composition comprising, for example, wheat germ lectin and cross-linked agarose wherein such binding interaction is disrupted by a liquid test sample containing N-acetylglucosamine.

(b) Interactive Matrix

The various layers described herein comprise a porous matrix which is permeable to analyte and critical test reagents, such permeability generally arising from porosity, ability to swell or any other characteristic. Although the test device layers can comprise various porous, fibrous materials such as cellulose, papers, fleeces, felts, woven fabrics and the like (see, for example, U.S. Pat. Nos. 3,802,842; 3,809,605; 3,897,214 and 3,987,213), or nonfibrous, porous materials such as microporous polymers (see, for example, U.S. Pat. No. 3,552,929), the matrix-forming materials of the test device layers which provide the reversible immobilization of assay reagents according to the present invention comprise synthetic polymers such as polyvinyl alcohol, polyvinyl-pyrrolidone, acrylamide polymers, sodium polyacrylate, polyhydroxyethyl methacrylate, copolymers containing acrylic acid or maleic acid, and the like; and hydrophilic colloids such as gelatin, agarose, sodium alginate, carboxymethyl cellulose, methyl cellulose, and the like. Permeable materials such as gelatin, agarose and the like are particularly preferred because of their uniform permeability to liquids, their ability to permit the passage of light or other electromagnetic radiation therethrough, and, as will be described in greater detail hereinafter, the ability to incorporate therein an insolubilized form of a binding substance having the desired reversible binding property for an assay reagent according to the present invention.

According to the present invention, the reversible immobilization of an assay reagent within the matrix of an incorporating layer is due to the reversible interactive binding properties which exist between an assay reagent and the matrix material. Although the matrix material preferably comprises a solid, porous, permeable material incorporated with an insolubilized form of a binding substance having the desired reversible interactive binding property for such reagent, matrix materials comprising a solid, porous, permeable material which have either been modified, e.g., chemically, biologically, or by incorporation of binding substances, to possess, or which inherently possess, the desired reversible interactive binding property for such assay reagent, can also be employed.

Although each of the various layers of a multilayer test device can be incorporated with reversibly immobilized assay reagents, it is to be understood that a multilayer test device can be constructed having one or more, but less than all, of such layers constructed according to the present invention. Accordingly, where less than all layers of a multilayer device are incorporated with one or more reversibly immobilized assay reagents according to the present invention, the matrix-forming materials of the other layers can be the same or different as those layers which are constructed according to the present invention. For example, where a multilayer test device comprises a reagent layer and a reaction layer employing agarose as a common matrix material, the matrix of only the reagent layer can be chemically or biologically modified, or can further include an insolubilized form of a binding substance, wherein the first reagent is reversibly immobilized thereto according to the present invention, while, at the same time, the matrix thereof will be consistent with the matrix material of the reaction layer.

Conversely, alternative matrix materials may be employed for the reversible immobilization of assay reagents in one layer, which alternative matrix materials could be different from the matrix materials of adjacent layers, resulting in a unique layer of an entirely different composition. However, where alternative matrix materials which are different from or unique with respect to adjacent or subsequent layers are employed instead of matrix materials which are consistent with each other as described above, it is essential that such alternative materials provide a satisfactory transport medium which is compatible with such other different layers in order to otherwise permit the free migration of assay reagents and the diffusion of fluids therebetween as heretofore described.

(i) Matrix incorporated with insolubilized binding substance.

The reversible immobilization of assay reagents within a particular layer of a multilayer test device is preferably accomplished by incorporating an insolubilized form of an interactive binding substance for such assay reagents within such layer. Such binding substance possesses the appropriate reversible interactive binding properties necessary for the reversible immobilization of an assay reagent thereto. Accordingly, the interactive binding substance must not only be a substance which can remain insolubilized within such layer under all fluid conditions, particularly while in the presence of a solvent during the manufacture of such layer, but must, at the same time, also provide for the reversible immobilization of an assay reagent thereto wherein the binding interaction between the assay reagent and the interactive binding substance is capable of being disrupted to release the assay reagent as heretofore described.

Depending upon the desired mechanism by which an assay reagent is to be reversibly immobilized to an interactive binding substance within a particular layer, e.g., ionic binding interactions, hydrophobic binding interactions, and the like, a number of interactive binding substances known in the art are available which can be employed for the incorporation thereof in such layer. Such interactive binding substances having an assay reagent reversibly immobilized thereto can be incorporated into a homogeneous suspension or emulsion of, for example, gelatin or agarose which can then be employed to form the desired layers according to methods known in the art, and include derivatized fibrous materials such as derivatized cellulose, derivatized synthetic polymers, and the like; derivatized granular materials such as derivatized Sephadex ®, derivatized latex microspheres, and the like; and derivatized microcrystalline materials such as derivatized microcrystalline cellulose and the like. Particularly preferred materials include anion exchange materials such as diethylaminoethyl cellulose, epichlorohydrin triethanolamine cellulose, triethylaminoethyl cellulose bromide, polyethyleneimine cellulose, quaternized ion exchanger cellulose, and the like; and cation exchange materials such as carboxymethyl cellulose, phosphate cellulose, and the like.

For example, where it is desired to reversibly immobilize a labeled reagent having an overall positive charge, e.g., an analyte or analog thereof labeled with a chromogenic dye such as rhodamine, within a particular layer comprising gelatin or agarose, such layer can be formed by incorporating a weakly acidic cation exchange material therein, such as carboxymethyl cellulose, having such labeled reagent reversibly immobilized thereto. Accordingly, upon application of a liquid test sample, such as whole blood or urine, to a test device comprising such layer, the physiological salts contained in the test sample will disrupt the reversible binding interaction between the carboxymethyl cellulose and the labeled reagent wherein the labeled reagent is released and thereby permitted to freely migrate into and through adjacent layers of such device to initiate the necessary interactions to generate a detectable signal as heretofore described.

Similarly, a labeled reagent having an overall negative charge can be employed, such as a fluorescein labeled anti-analyte antibody conjugate wherein a weak anion exchange material such as diethylaminoethyl cellulose would be employed as the insolubilized interactive binding substance in such incorporating layer.

Lectins, which are proteins or glycoproteins of a non-immune origin, are particularly useful for establishing a reversible biochemical binding affinity between an assay reagent and the matrix of a particular layer of a multilayer test device according to the present invention. Such reversible biochemical binding affinity can be between the assay reagent and lectins which have been immobilized onto a solid support such as wheat germ lectin-Sepharose ® 6MB, helix pomatia lectin-Sepharose ® 6MB, lentil lectin-Sepharose ® 4B, and the like. Other insolubilized interactive binding substances capable of providing a reversible biochemical binding affinity for an assay reagent include concanavalin A-Sepharose ® 4B, cibacron blue-Sepharose ® CL-6B, lysine-Sepharose ® 4B, and the like.

Similarly, an assay reagent can be reversibly immobilized by a reversible biochemical binding affinity involving hydrogen bonding between an assay reagent and an interactive binding substance. Such interactive binding substances can be immobilized onto a solid support and include polyuridylic acid-Sepharose ® 4B, polyadenylic acid-Sepharose ® 4B, and the like.

In addition, other reversible binding interactions include reversible covalent binding interactions involving, for example, an assay reagent reversibly immobilized to thiopropyl-Sepharose ® incorporated into an agarose matrix, and hydrophobic binding interactions involving a binding interaction between an assay reagent and hydrophobic supports such as phenyl-Sepharose ® 4B, octyl-Sepharose ® 4B, hexyl-Sepharose ® 4B, and the like.

It is to be appreciated that the particular reversible binding interactions established with the interactive binding substances heretofore described are disrupted with specific liquid test samples and/or diluents, as will be described in greater detail hereinafter.

(ii) Modification of the matrix material.

Alternatively, a matrix material or composition can be chemically modified with a reactive group to possess the desired reversible interactive binding properties for a particular assay reagent in order to reversibly immobilize such assay reagent therein. Such modification would provide the necessary binding interaction between the matrix and the assay reagent to reversibly immobilize the assay reagent therein without the need to incorporate an additional interactive binding substance, such as a fibrous or microcrystalline material as heretofore described, to thereby provide the same function as the interactive binding substances described above.

The modification of a matrix material or composition for the reversible immobilization of an assay reagent thereto is accomplished by chemically linking or coupling interactive binding substances or reactive groups directly to the matrix material or composition. It is to be appreciated that the reactive groups can be chemically linked or coupled to matrix materials such as, for example, gelatin or agarose, according to methods known in the art, and can be any reactive group capable of providing the necessary reversible interactive binding properties as heretofore described. Such reactive groups include ionic reactive groups such as diethylaminoethyl, epichlorohydrin, triethylaminoethyl, carboxymethyl and phosphate substituents, and the like; hydrophobic reactive groups such as phenyl, octyl and hexyl substituents, and the like; reversible covalent groups such as thiopropyl substituents and the like; and reversible biochemical binding affinity binding groups such as concanavalin A, avidin, 5'-adeninemonophosphate, 2',5'-adeninediphosphate, lysine, polyuridylic acid, polyadenylic acid, and the like.

(c) Liquid Test Sample.

The liquid test sample containing the analyte under determination can be a naturally occurring or artificially formed liquid suspected to contain analyte, and is usually a biological fluid or a dilution thereof, depending upon the required disruptive properties thereof necessary to disrupt a particular reversible interactive binding interaction between the matrix and the assay reagent. Biological fluids from which analyte can be determined include serum, whole blood, plasma, urine, saliva, and amniotic and cerebrospinal fluids.

The nature of the liquid test sample will depend upon the nature of the particular binding interaction which exists between the matrix and the reversibly immobilized assay reagent and the necessary disruptive properties of such liquid test sample therefor. Typically, where the liquid test sample is a biological fluid, the nature of the binding interaction between the matrix and the assay reagent or reagents reversibly immobilized thereto is weakly ionic in nature, i.e., anionic or cationic, wherein the binding interaction therebetween is disrupted by the relatively low, physiological salt concentration of such biological test sample to thereby release and permit the migration of such assay reagent or reagents for the participation thereof in the necessary assay interactions within the test device.

However, it is to be appreciated that the liquid test sample is not intended to be limited to an undiluted biological test sample, but can be a mixture of a biological test sample and a diluent or additive, such as a physiological salt solution, capable of disrupting the binding interaction between a particular matrix and an assay reagent or reagents. The choice of diluent or additive to be employed, of course, will depend upon the particular binding interaction between the matrix and assay reagent in determining the disruptive properties of such diluent for such binding interaction. For example, where the reversible binding interaction is ionic in nature as heretofore described, further to the disruptive properties of an undiluted biological test sample for such binding interaction, a diluent such as physiological saline (e.g., 00 mM phosphate buffered saline) can be added to a test sample to disrupt such binding interaction between an assay reagent and a matrix material comprising, for example, diethylaminoethyl cellulose or carboxymethyl cellulose.

Similarly, where a hydrophobic binding interaction exists between a particular matrix and an assay reagent, such binding interaction is disrupted by decreasing the ionic strength of the liquid test sample, or, for example, by decreasing the polarity of the test sample. The polarity of a liquid test sample can be decreased by adding a non-ionic detergent such as NP-40® or Tween ®, or by adding ethylene glycol, to the test sample.

It is to be appreciated that in certain instances, specific binding interactions involving reversible biochemical binding affinities between an assay reagent and an interactive binding substance or matrix material require the presence of a specific diluent or additive in the test medium comprising a competing ligand which is capable of binding to an insolubilized form of a binding substance for the ligand or a ligand receptor incorporated into the reagent layer. In such instance, the labeled assay reagent is also conjugated with such ligand wherein the ligand of the assay reagent competes with the competing ligand diluent or additive for binding to the binding substance for the ligand or ligand receptor. It is to be understood that under such conditions of competition, binding of the competing ligand to the binding substance or receptor therefor prevents the assay reagent from binding to the binding substance to thereby permit the free migration thereof into the detection layer.

In particular, reversible biochemical binding affinity interactions involving binding interactions with binding substances such as concanavalin A, wheat germ lectin, helix promatia lectin, lentil lectin, monomeric avidin, 5'-adeninemonophosphate or 2',5'-adeninediphosphate, and lysine, are specifically disrupted with competing ligands such as α-methylmannoside, N-acetyl glucosamine, N-acetyl α-D-galactosamine, methyl α-D-mannoside or methyl α-D-glucoside, derivatized biotin such as desthiobiotin, diaminobiotin, or 2-iminobiotin, nicotinamide adenine dinucleotide or nicotinamide adenine dinucleotide phosphate, and e-aminocaproic acid, respectively.

Other reversible biochemical binding affinity interactions include the reversible biochemical binding affinity between polyuridylic acid or polyadenylic acid and an assay reagent which is specifically disrupted by a buffer solution containing formamide, as well as the reversible covalent binding interaction between, for example, a thiopropyl substituent and an assay reagent which is specifically disrupted by L-cysteine, dithiolthreitol, β-mercaptoethanol, or other thiol reducing agents.

Multilayer Analytical Elements

The reversible immobilization of assay reagents according to the present invention can be applied to most any multilayer test device involving either immunoassay or non-immunoassay test formats which require the participation of one or more assay reagents in an assay reaction system for the determination of analyte from a liquid test sample wherein such assay reagents must be prevented from prematurely migrating and interacting with each other prior to application of a liquid test sample thereto. The incorporation of such assay reagents during the formation of various layers for use in the assembly of a multilayer test device permits the fixation of such layers into a laminar relationship with one another without the necessity of drying each layer prior to the lamination of one layer with another. This is particularly advantageous over the prior art methods of manufacturing multilayer test devices, as described above, wherein the various layers formed according to such methods must be dried before the lamination to prevent the solubilization and subsequent premature interaction of assay reagents incorporated therein. Depending upon the particular assay format, all or some of the necessary assay reagents can be reversibly immobilized in one or more of such layers according to the present invention. Where less than all of the necessary assay reagents are reversibly immobilized according to the present invention, the remaining assay reagents can be incorporated in a soluble form in one or more of such layers, or can be immobilized according to methods known in the art. It is to be appreciated, however, that where some of such assay reagents are incorporated in a soluble form, such assay reagents must be incapable of prematurely interacting with other assay reagents prior to application of a liquid test sample thereto.

According to the present invention, multiple layers incorporated with one or more reversibly immobilized assay reagents can be assembled simultaneously, or sequentially, using film formers to prepare consecutive over-laying coatings, or by superimposing layers of a fibrous matrix such as filter paper, glass fiber or woven polyester, prior to drying each layer thereby formed. Alternatively, multiple consecutive layers can be cast simultaneously with a cascade coater. The reversible immobilization of assay reagents in such layers or zones prevents the solubilization of such assay reagents by, for example, the solvent employed during the formation of a subsequent adjacent layer which diffuses into the previously formed adjacent layer or layers to otherwise result in the solubilization and premature migration of assay reagents therein and therebetween.

The nature of the particular assay reagents to be reversibly immobilized into one or more layers of a multilayer test device will depend upon the particular assay format, i.e., non-immunoassay or immunoassay format. For instance, where the assay involves a non-immunoassay type format, such as for the detection of a transaminase in a liquid test sample, the necessary assay reagents for detecting transaminase activity can be incorporated into a multilayer test device according to the present invention. Typically, the detection of transaminase activity involves an initial reaction between an aminoacid and a keto-acid in the presence of a transaminase catalyst which results in the formation of, for example, pyruvic acid, and the subsequent measurement thereof with an appropriate substrate therefor and indicator system which can then be correlated to the amount of transaminase in the liquid test sample. Under such reaction conditions, it is necessary to isolate the keto-acid from free amine groups and/or reagents containing free amine groups to prevent the premature interaction thereof prior to application of the liquid sample to the test device. Accordingly, the keto-acid can be reversibly immobilized in the reagent layer according to the present invention, and the remaining assay reagents incorporated into subsequent layers of such test device.

Similarly, assay reagents which are necessary for performing a specific binding assay, such as an immunoassay, can be incorporated into the various layers of a multilayer test device according to the present invention. The specific binding assay determination of analyte from a liquid test medium typically involves binding among the analyte, a reversibly immobilized labeled reagent, and a binding partner of the analyte, or the analyte or binding analog thereof. The labeled reagent comprises the analyte or binding analog thereof, or a binding partner of the analyte, respectively, depending upon the nature of the immobilized reagent, labeled with a detectable chemical group having a detectable chemical or physical property as heretofore described. Under such reaction conditions involving interactive immunoassay reagents, it is necessary to prevent the premature interaction of the labeled reagent and the appropriate detection system reagents for such labeled reagent prior to application of the liquid test sample to such test device. Accordingly, the labeled reagent can be reversibly immobilized in the reagent layer according to the present invention, and the detection system reagents can be incorporated into subsequent layers of such test device, as will be described in greater detail hereinafter.

Preferably, the second reagent, or other assay reagents which are similarly capable of interacting with the first reagent to provide a detectable signal, are incorporated into a detection layer in an immobilized form according to methods known in the art. Unlike the first reagent which is reversibly immobilized according to the present invention as heretofore described, such immobilized assay reagents are not capable of being solubilized or otherwise removed from such layer upon contact with the liquid test medium or other liquid reagents. Accordingly, the immobilization of such assay reagents prevents the premature migration thereof into adjacent and subsequent layers of a test device which would otherwise result in the premature interaction of assay reagents and/or the subsequent generation and detection of an interfering, non-specific signal.

In particular, where an assay reaction or interaction involves a labeled reagent comprising a chemical group having a detectable chemical property as heretofore described, such as an enzyme, the interaction, for example, of the enzyme with a second reagent, such as a substrate for the enzyme, incorporated into the detection layer, results in the generation of a reaction product which either inherently provides a detectable signal, or requires further interaction with another substance or other substances to provide a detectable signal, depending upon the nature of the label of the labeled reagent and the second reagent. It is to be appreciated that the reaction product can also be inherently immobilized as a result of the immobilization of the labeled reagent and the second reagent, or can be generated in a soluble form which can be immobilized by an immobilized binding agent in the detection layer having a binding affinity for the reaction product. Such immobilized binding agent can also be an immobilized substance necessary for the generation of a detectable signal upon interacting with the reaction product where the reaction product does not inherently provide a detectable signal as heretofore described.

Similarly, where the labeled reagent comprises a chemical group having a detectable physical property as heretofore described, such labeled reagent can further include a binding site for the second reagent which comprises a binding substance or binding counterpart for the binding site of the labeled reagent. Accordingly, selection of an appropriate binding substance for immobilization in the detection layer necessarily depends upon the selective recognition for such binding site by such binding substance. For example, the labeled reagent comprises a ligand moiety which forms a specific binding pair with the binding substance. In particular, preferred representative binding pairs for the ligand moiety and the binding substance include such binding pairs as haptens and antibodies, or fragments thereof, to such haptens; biotin and avidin; carbohydrates and lectins; and antibody, or fragment thereof, having an intact binding site for Protein A and Protein A; and the like. Additional binding pairs include complementary single stranded oligonucleotide sequences; effector molecules and receptor pairs; prosthetic groups and apoprotein; enzyme cofactors and enzymes; polymeric acids and bases; dyes and protein binders; peptides and specific protein binders (e.g., ribonuclease, S-peptide and ribonuclease S protein); enzyme inhibitors (reversible and irreversible), enzymes and the like.

Further, the labeled reagent can be selectively immobilized by binding to an adsorbent material for the labeled reagent, such as an ion exchange material, which acts as the binding substance which is immobilized in the detection layer. Other materials may also be employed as a binding substance for the first or labeled reagent provided, of course, that the binding site on the labeled reagent and the binding substance have selectivity for binding each other and would not be subject to substantial non-specific binding to other reagents within the assay system.

Generally, such multilayer test device comprises (i) a reagent layer incorporated with the reversibly immobilized labeled reagent according to the present invention, (ii) a reaction layer incorporated with an immobilized or insolubilized form of a binding partner of the analyte, such as an antibody thereto, where the labeled reagent comprises a labeled form of the analyte or binding analog thereof, or an immobilized or insolubilized form of the analyte or binding analog thereof where the labeled reagent comprises a labeled form of a binding partner of the analyte, and (iii) a detection layer for receiving and measuring any of the analyte-bound labeled reagent which migrates therein.

It is to be appreciated that according to the present invention, the reversibly immobilized labeled reagent in the reagent layer remains immobile prior to application of the liquid test sample to the test device, which liquid test sample possesses the necessary interactive properties for disrupting the reversible binding interaction between the labeled reagent and the matrix of the reagent layer as heretofore described. Accordingly, upon application of the liquid test sample to the test device, the liquid test sample diffuses into the reagent layer and interacts with, and disrupts the binding interaction between, the labeled reagent and the reagent layer matrix to thereby release an analytically effective amount of freely diffusible labeled reagent therein. At the same time, analyte from the liquid test sample is permitted to mix with the labeled reagent and the mixture proceeds to migrate from the reagent layer into and through the reaction layer, and into the detection layer where the label of the labeled reagent is detected and correlated to the amount of analyte in the liquid test sample.

Various methods known in the art are available for the permanent immobilization of reagents other than the reversibly immobilized reagent, such as in the reaction layer or detection layer of the test device of the present invention. Immobilization through covalent attachment of the reagent can be used as well as other means which utilize non-covalent association. Immobilization of reagents can be achieved, for example, by direct incorporation into the carrier matrix of the device, such as cellulose in paper, or into gelatin or agarose in films. Alternatively, the reagents can be linked to a polymeric carrier which is then subsequently incorporated into the matrix of the device, the polymer being of sufficient size to prevent significant diffusion between the binding and detection layers. In gelatin, for example, polymers greater than 10,000 in molecular weight will exhibit negligible diffusion through the gelatin matrix. The reagents can also be linked directly or via a polymer backbone to very small particles such as polystyrene microbeads which can then be subsequently incorporated into the matrices of the device. Such particles are readily available in a range of sizes and include polystyrene, microcrystalline cellulose, cross-linked dextrans and cross-linked agaroses, and the like. A wide range of chemistries are available to couple reagents onto the carrier which are well-known in the art.

It is to be appreciated that except for reflecting layers and radiation-blocking agents, as will be described in greater detail hereinafter, the various zones or layers and supports of the present invention are radiation-transmissive in most instances. Such zones or layers and supports permit effective passage of visible light, fluorescent or luminescent emission, radioactive radiation, and the like. The choice of a particular radiation-transmissive material will depend upon the particular radiation selected for use with an element in which the material is to be incorporated.

Detection of the signal produced by the label can be accomplished with the use of an appropriate instrument, such as a spectrophotometer, i.e., reflectometer, fluorometer or luminometer. For example, where detection is based upon absorbance or fluorescence, a beam of energy from such instrument is directed either at and through the reagent layer or at and through the reaction layer, or at and through the detection layer when such layer is provided. On the other hand, where detection is based upon luminescence, an appropriate instrument which detects such luminescence without the need of an energy source is utilized.

Although the various layers of the multilayer device of the present invention can be self-supporting, it is preferred that such layers be coated or otherwise positioned onto a support member. The support member can be opaque, reflective, or transparent to light or other energy. A support member of choice for the various layers will be compatible with the intended mode of signal detection. For example, where the chemistry of the test device generates a gaseous product for detection thereof with a gas sensing electrode, the support member is a fluid permeant layer in liquid contact with such electrode. Preferred support members include transparent support materials capable of transmitting electromagnetic radiation of a wavelength within the region between about 200 nm and about 900 nm. The support need not, of course, transmit over the entire 200-900 nm region, although for fluorometric detection of analytical results through the support it is desirable for the support to transmit over a wider band or, alternatively, to transmit at the excitation and emission spectra of the fluorescent materials used for detection. It may also be desirable to have a support that transmits over a narrow wavelength band width and which has reduced transmittance to adjacent wavelengths. This could be accomplished, for example, by impregnating or coating the support with one or more colorants having suitable absorption characteristics.

A radiation-transmissive or transparent support member permits a beam of energy, such as light, to pass therethrough. The beam is then either reflected, such as from a radiation-blocking layer as will be described in greater detail hereinafter, back to a sensing component of the instrument, or transmitted through the device to a sensing component of the instrument. Where an opaque or reflective support member is utilized, a beam of energy is directed through the various layers of the device and reflected by the reflective layer back to a sensing component of the device.

For example, and referring now to the figures, there is illustrated in FIG. 1 a multilayer immunoassay test device comprising a reagent layer incorporated with a reversibly immobilized labeled reagent comprising an enzyme-labeled anti-analyte antibody, a reaction layer incorporated with an immobilized form of analyte or analog thereof, and a detection layer incorporated with an immobilized form of a substrate for the enzyme, all of which are mounted onto or otherwise positioned onto a reflective support member. It will be appreciated that the immobilized form of analyte in the reaction layer, as well as the immobilized form of the substrate in the detection layer as heretofore described, are not capable of being solubilized or otherwise removed from their respective layers upon contact with the liquid test sample which diffuses therein.

Upon application of the liquid test sample to the reagent layer, the test sample diffuses into the reagent layer to disrupt the reversible binding interaction between the labeled reagent and the reagent layer matrix wherein the analyte from the test sample becomes bound to the antibody thereto of the labeled reagent and wherein the analyte-labeled antibody complex thereby formed is free to migrate into and through the reaction layer and into the detection layer. Labeled reagent not bound to analyte from the test sample becomes immobilized by binding to the immobilized reagent in the reaction layer. The enzyme of the analyte-labeled antibody complex which migrates into the detection layer reacts with the substrate to produce the formation of a detectable product, e.g., fluorescent or luminescent, which preferably remains confined to the detection layer.

To measure the desired enzyme-substrate reaction, a beam of energy is directed through the reagent layer, the reaction layer and the detection layer, respectively, where the beam is then reflected back to the sensing means of the instrument by the reflective support member. The nature of the beam which passes through the various layers and reflected by the support member is affected by the amount of product within the detection layer wherein a detectable change in the beam is correlated to the amount of analyte in the test medium. It is to be appreciated that since the detectable signal is produced only upon the enzyme-substrate reaction, there is no need for a radiation-blocking layer or the like since there is no interfering signal such as would be the case where a chemical group having a detectable physical property is utilized. In this respect, the beam of energy is affected only by the reaction product of the enzyme-substrate reaction.

Figure 2:
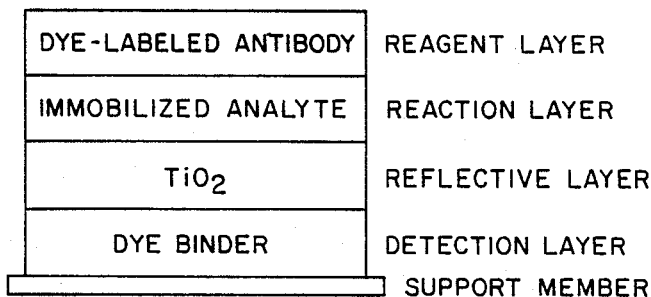
FIG. 2 is a sectional view of a multilayer test device incorporated with reversibly immobilized assay reagents according to the present invention for performing an immunoassay involving a dye-labeled antibody as one of the assay reagents.

Conversely, where the binding partner is labeled with a chemical group having a detectable physical property, it is necessary to provide a device which prevents detection of the signal produced by any of the excess labeled binding partner which becomes bound by the immobilized analyte in the reaction layer. Such a device is illustrated by FIG. 2 which includes a reagent layer incorporated with a reversibly immobilized binding partner, i.e., anti-analyte antibody, labeled with a dye, a reaction layer incorporated with an immobilized form of the analyte or analog thereof, and a detection layer incorporated with an immobilized form of a binder for the dye conjugate which localizes the signal of the analyte-bound labeled binding partner which migrates from the reagent layer into the detection layer. The various layers are mounted or otherwise positioned onto a transparent or radiation-transmissive support member through which a beam of energy is directed. It is to be appreciated that since any of the labeled binding partner which does not become bound to the analyte from the test sample will be immobilized in the reaction layer, it is necessary to prevent detection of the signal produced therefrom. This is accomplished by incorporating a radiation-blocking and/or reflecting substance into the reaction layer, or, alternatively, interposing a radiation-blocking and/or reflecting layer between the reaction layer and the detection layer. Accordingly, when a source of energy is directed through the radiation-transmissive support member and into the detection layer, the energy is absorbed or reflected back through the detection layer and support member by the radiation-blocking substance or layer and thereby affected by the label which is present in the detection layer, but not by the label from the immobilized labeled binding partner in the reaction layer.

The reflective layer is optionally absorptive to detecting radiation such as to facilitate signal detection by reflection radiometry, e.g., reflection photometry, fluorescence, or a similar technique. By incorporating such layer between the reaction and detection layers, any signal produced from the analyte-bound labeled binding partner in the detection layer would be detected without an interfering signal produced by the immobilized-unbound labeled binding partner in the reaction layer as a result of such non-transmissive reflective layer incorporated therebetween. In this manner, the signal produced by each layer can be detected, measured, and correlated to the amount of analyte in the liquid test medium.

Alternatively, it may be desirable to utilize radiation-blocking agents which would be incorporated into the reaction layer. Reflective pigments, such as titanium dioxide, barium sulfate or zinc oxide can be used for this purpose. Blush polymers can also be used, either independently, or incorporated with a reflective pigment to enhance reflectivity or other properties. Such radiation blocking layers and agents are known in the art and include those described in U.S. Pat. Nos. 4,042,335 and 4,255,384.

Where a fluorophore is used as the label in the labeled reagent, the detectable signal can be alternatively masked from the detection system by use of quenching phenomenon without need for radiation-blocking layers or materials. Those layers or zones in which the signal is to be blocked, e.g., the reagent layer when measuring in the detection layer, can be incorporated with an immobilized substance that effectively quenches the fluorescence of the label as a result of changes in media polarity or incorporation of quenching groups such as heavy atoms, e.g., iodine.

Figure 3:
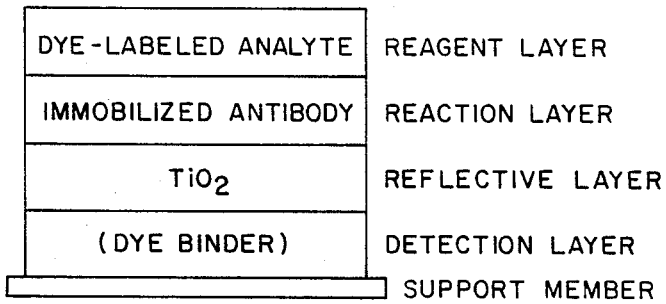
FIG. 3 is a sectional view of a multilayer test device incorporated with reversibly immobilized assay reagents according to the present invention for performing an immunoassay for the detection of an analyte involving dye-labeled analyte as one of the assay reagents.

Referring now to FIG. 3, there is illustrated therein a multilayer test device comprising a reagent layer incorporated with a reversibly immobilized dye-labeled analyte conjugate, a reaction layer incorporated with an immobilized form of an anti-analyte antibody, a reflective layer, and a detection layer for receiving and measuring dye-labeled analyte conjugate which migrates therein, and which can be optionally incorporated with an immobilized form of a binder for the dye conjugate, all of which are mounted or otherwise positioned onto a transmissive support member. Upon application of a liquid test sample containing analyte to the reagent layer, the liquid test sample diffuses into the reagent and reaction layers, as well as into the detection layer, to interact with and disrupt the reversible binding interaction between the labeled conjugate and the reagent layer matrix to release and thereby render diffusible an analytically effective amount thereof within the test device.

According to this particular immunoassay format, analyte from the test sample competes with the released dye-labeled analyte conjugate from the reagent layer for binding to the anti-analyte antibody immobilized in the reaction layer. Any of the analyte from the test sample or dye-labeled analyte conjugate which binds to the immobilized anti-analyte antibody is prevented from further migrating out of the reaction layer and, conversely, when not so bound, are permitted to migrate into the detection layer. The label of the conjugate which migrates into the detection layer is detected and correlated to the amount of analyte in the test sample. It is to be appreciated that where a binder for the dye conjugate is optionally immobilizied in the detection layer, the dye conjugate becomes bound to the binder and thereby localizes the signal generated by the dye conjugate therein.

Other immunoassay formats include, but are not intended to be limited to, the detection of analyte employing a flavin adenine dinucleotide (FAD) labeled analyte conjugate in an immunoassay system, such as that described in U.S. Pat. No. 4,493,890 and assigned to the assignee of the present invention, incorporated into a multilayer test device such as that which is illustrated in FIG. 4, and the detection of analyte employing a chromogenic analyte conjugate in an immunoassay system incorporated into a multilayer test device such as that which is illustrated in FIG. 5.

Figure 4:
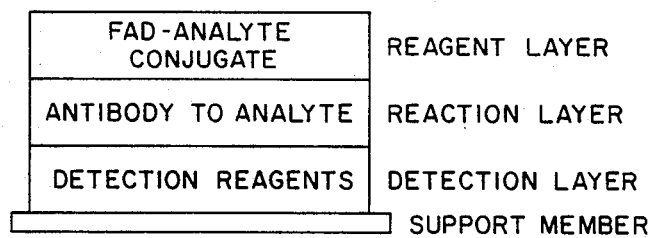
FIG. 4 is a sectional view of a multilayer test device incorporated with reversibly immobilized assay reagents according to the present invention for performing an immunoassay for the detection of an analyte involving FAD-labeled analyte as one of the assay reagents.

In particular, the multilayer test device in FIG. 4 comprises a reagent layer incorporated with a reversibly immobilized FAD labeled-analyte conjugate, a reflective layer, a reaction layer incorporated with a reversibly immobilized antibody to analyte, and a detection layer incorporated with detection reagents which include apoglucose oxidase, peroxidase, glucose, and an indicator composition that provides a chromogenic response to hydrogen peroxide in the presence of peroxidase. Upon addition of test sample and resulting release of the FAD-analyte conjugate, the mixture migrates to the reaction layer where analyte and labeled analyte compete for binding to the antibody. FAD-analyte conjugate that does not become bound continues to migrate into the detection layer where the FAD portion of the conjugate activates apoglucose oxidase. Resulting glucose oxidase acts on glucose to produce hydrogen peroxide which causes a chromogenic response on the indicator composition related to the concentration of analyte in the sample.

Figure 5:
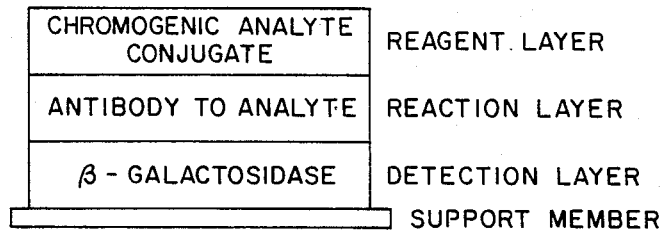
FIG. 5 is a sectional view of a multilayer test device incorporated with reversibly immobilized assay reagents according to the present invention for performing an immunoassay for the detection of an analyte involving analyte labeled with a chromogenic substrate material as one of the assay reagents.

The multilayer test device in FIG. 5 comprises a reagent layer incorporated with a reversibly immobilized chromogenic analyte conjugate, such as analyte labeled with a chromogenic substrate material, an optional reflective layer to intensify the signal generated in the detection layer, a reaction layer incorporated with a reversibly immobilized antibody to analyte, and a detection layer incorporated with an immobilized form of an enzyme capable of acting on the substrate to release a chromogen, mounted or otherwise positioned onto a transmissive support member. Here again, upon application of the test sample, the released labeled conjugate mixes with analyte from the test sample and migrates to the reaction layer where they compete for binding to antibody. Labeled reagent that does not become bound to the antibody in the reaction layer, continues migrating to the detection layer where it is acted on by the enzyme to produce a chromogenic signal related to the concentration of analyte in the sample.

It is to be appreciated that the various layers of the multilayer test device of the present invention are not limited to the layers and configurations as heretofore described. Additional layers for use with the multilayer test device have been described and are known in the art which enhance and/or modulate the performance of such test devices. For example, a spreading zone or layer could be included which would be positioned immediately above and adjacent to the reagent layer. The spreading zone meters and evenly distributes an applied liquid test sample to the underlying reagent zone. Such spreading zones or layers are known in the art and include those described in U.S. Pat. Nos. 3,992,158 and 4,427,632.

The device can also include an intermediate zone or layer between the various layers which serves as an adhesive or subbing layer to facilitate adhesion between the layers and to further facilitate adhesion of the layers to a solid support member. Intermediate zones or layers can also be employed which, for example, contain reagents for removing interferants which may prevent detection of some of the analyte or, can be a radiation-blocking zone or layer which masks zones or layers of the device to prevent interference in detection of the product. Such radiation-blocking layers can also be employed which mask the presence of various interfering substances found in test samples, such as red cells in whole blood. An intermediate zone or layer such and that described in U.S. Pat. No. 4,166,093 can also be employed which inhibits or prevents undesired back-migration of a detectable substance from the reagent zone into the spreading layer where the detectable substance may become masked or otherwise difficult to detect.

The device of the present invention can also be a multizone device having reagent zones, detection zones, and the like assembled in a configuration particularly adapted for chromatographic analysis. Such a device would include an absorbent region which would be immersed into the liquid test medium wherein the test medium would diffuse in an upward direction into the various zones.

The zones of such multizone test device are in the form of reagent pads which are mounted onto a plastic support member adapted to be immersed or dipped into a liquid test medium. The zone-forming reagent pads are positioned onto the support member in an end to end relationship wherein the ends thereof are in fluid flow contact with one another. In particular, such reagent pads include a lowermost, liquid test medium-absorptive pad or zone, reagent and reaction pads or zones, respectively, positioned thereabove, and a detection pad or zone positioned above the reaction zone.

It is to be appreciated that the reagent, reaction and detection zones are incorporated with the various reagents of the multilayer test device previously described and perform the same functions thereof. In this embodiment, however, instead of a liquid test medium sample being applied to the test device, the lowermost absorptive pad of the multizone test device is immersed into the liquid test medium. In this manner, the absorptive pad serves as a wick for the absorption of the test medium and the upward diffusion thereof into the reagent zone, the reaction zone, and the detection zone, respectively. Devices in configurations such as described in U.S. Pat. Nos. 4,301,139 and 4,361,537 involving the use of developing fluids can also be adapted to the present invention.

The present invention will now be illustrated, but is not intended to be limited, by the following example:

EXAMPLE

Reversible Immobilization of Cationic Dye-Labeled Analyte to Anionic Reagent Layer Matrix (a) Cationic Dye-Labeled Analyte Conjugate.

A solution of 24.2 mg (54 μmol) 8-[carboxypropyl-(bis-N,N-3-aminopropylpiperazine)]theophylline trihydrochloride hydrate dissolved in 5 ml anhydrous dimethylacetamide (Aldrich Chemical Co., Milwaukee, Wis., U.S.) and 15 μl triethylamine (Aldrich Chemical Co., Milwaukee, Wis., U.S.) was stirred overnight at room temperature as a reaction mixture with 24 mg (54 μmol) tetramethylrhodamine isothiocyanate (Research Organics, Cleveland, Ohio, U.S.). The progress of the reaction was monitored on thin layer chromatography silica gel plates developed with a mixture of 95:5 (v/v) methanol and triethylamine. After 24 hours, the reaction was terminated by removing the solvent of the reaction mixture on a rotary evaporator, and the rhodamine-conjugate product (tetramethylrhodamine isothiocyanato-8-[carboxypropyl-(bis-N,N-3-aminoopropylpiperazine)]theophylline) was isolated by flash chromatography on a 2.5×30 cm column of Merck silica gel, grade 60, 230–400 mesh, 60 Å (Aldrich Chemical Co., Milwaukee, Wis., U.S.) equilibrated with methanol. The column was eluted first with 1000 mL methanol and then with 1000 mL of a 95:5 (v/v) mixture of methanol-triethylamine and the rhodamine-conjugate product collected.

(b) Anionic Reagent Layer Matrix.

A microgranular form (30–60 μ) of carboxymethyl cellulose (Whatman CM-52, Whatman, Inc., Clifton, N.J., U.S.) was washed in 0.2 M acetic acid, and then washed in deionized water. 1.0 mM rhodamine conjugate from step (a) was added to equal volumes of a 50% slurry of the washed carboxymethyl cellulose in deionized water and incubated for 5 minutes at room temperature. The rhodamine-conjugate solution was washed with deionized water and added as a wet-cake to approximately 3 volumes of a solution of 0.2% agarose (IEF grade, Pharmacia, Inc., Piscataway, N.J., U.S.) and 0.1% TRITON ® X-100 (Sigma Chemical Co., St. Louis, Mo., U.S.) and mixed as a slurry for approximately 30 seconds at 50° C.

(c) Multilayer Test Device.

A multilayer test device was prepared utilizing a transparent support member (Trycite ®, Dow Chemical Co., Midland, Mich.) and forming thereon, respectively, a detection layer of 10% gelatin (American Scientific Company, McGaw Park, Ill., U.S.) and 0.1% Triton ® X-100 layered to a wet-thickness of 300 μm, a reflective layer of 30% titanium dioxide (J. T. Baker Chemical Co., Philipsburg, N.J., U.S.) dispersed in 10% gelatin and 0.1% Triton ® X-100 layered to a wet-thickness of 60 μm, a second upper layer of 5% gelatin, 0.5% Calgon (Calgon Corp., Pittsburgh, Pa., U.S.) 0.016% sodium dodecyl benzene sulfonate (Aldrich Chemical Co., Milwaukee, Wis., U.S.) and 0.1% Triton ® X-100 layered to a wet-thickness of 100 μm, a first upper layer of 1.0% agarose and 0.1% Triton ® X-100 layered to a wet-thickness of 20 mil, and the rhodamine-conjugate slurry from step (b) layered thereon to a wet-thickness of 20 mil. The test device was then dried under a cool stream of air until completely dried (approximately 30 minutes). Upon drying, the pink coloration of the rhodamine-conjugate was visible from the reagent layer of the test device, whereas essentially no pink coloration was visible from the detection layer of the test device, indicating that the rhodamine-conjugate remained reversibly immobilized in the reagent layer during the wet lamination and drying processes.

(d) Operation of the Test Device.

A 50 μl sample of a liquid test medium solution of phosphate buffered saline (pH 7.5) was applied to the reagent layer matrix to disrupt the ionic binding interaction between the rhodamine-conjugate and the matrix to release and render diffusible the rhodamine-conjugate within the reagent layer. The rhodamine-conjugate was then permitted to diffuse and migrate into and through the adjacent layers and into the detection layer where the optical signal (pink coloration) provided by the rhodamine label of the rhodamine-conjugate was clearly visible. After completion of the reaction (approximately 60 seconds), essentially no pink coloration was visible from the reagent layer of the test device, indicating the release and subsequent diffusion of substantially all of the rhodamine-conjugate into the detection layer.

What is claimed is:

1. A multizone test device for the immunoassay determination of an antigen or hapten analyte in a liquid test medium, comprising, in fluid flow contact, (a) a reagent zone comprising a solid, porous matrix and a labeled reagent reversibly immobilized therein by a binding interaction between the labeled reagent and the matrix that is sufficiently disruptable by contact of the matrix with a predetermined component of the test medium other than the analyte to release and thereby render diffusible an analytically effective amount of the labeled reagent independent of the presence or amount of analyte in the liquid test medium, the labeled reagent comprising one of the pair
   (i) the analyte or a binding analog thereof, and
   (ii) an antibody which binds the analyte labeled with a detectable chemical group,
 (b) a reaction zone comprising a solid, porous matrix incorporated with an immobilized form of the other of said pair which interacts with both of the analyte and the labeled reagent to bind and thereby immobilize labeled reagent while leaving an amount of the labeled reagent diffusable as a function of the amount of analyte in the liquid test medium, and
 (c) a detection zone comprising a solid, porous matrix for receiving labeled reagent which is free to diffuse thereinto from the reaction zone to provide a detectable signal related to the amount of analyte present in the liquid test medium.

2. The test device of claim 1 wherein the reversible binding interaction is an anionic binding interaction between the labeled reagent and the reagent zone matrix and wherein the liquid test medium comprises a salt solution.

3. The test device of claim 2 wherein the reagent layer matrix comprises an ion exchange material.

4. The test device of claim 3 wherein the ion exchange material is an anion exchange material selected from the group consisting of diethylaminoethyl cellulose, epichlorohydrin triethanolamine cellulose, triethylaminoethyl cellulose bromide and polyethyleneimine.

5. The test device of claim 3 wherein the ion exchange material is a cation exchange material selected from the group consisting of carboxymethyl cellulose, phosphate cellulose and dextran sulfate.

6. The test device of claim 1 wherein the reversible binding interaction is a reversible covalent binding interaction between the labeled reagent and the reagent zone matrix and wherein the liquid test medium comprises a reducing agent.

7. The test device of claim 1 wherein the reversible binding interaction is a hydrophobic binding interaction between the labeled reagent and the reagent zone matrix and wherein the liquid test medium comprises a non-ionic detergent.

8. The test device of claim 1 wherein the reversible binding interaction is a reversible biochemical binding affinity between the labeled reagent and the reagent zone matrix and wherein the liquid test medium comprises a competing ligand.

9. The test device of claim 1 wherein the liquid test medium comprises an undiluted biological fluid test sample capable of disrupting the binding interaction between the reagent zone matrix and the labeled reagent.

10. The test device of claim 1 wherein the liquid test medium comprises a mixture of a biological fluid test sample and a diluent capable of disrupting the binding interaction between the reagent zone matrix and the first reagent.

11. The test device of claim 1 wherein the biological liquid test medium is whole blood, blood serum, blood plasma, amniotic fluid, cerebrospinal fluid or urine.

12. The test device of claim 1 wherein the detectable chemical group of the labeled reagent is coupled to the analyte, binding analog, or antibody by a linking group.

13. The test device of claim 12 wherein the reversible binding interaction is between the matrix of the reagent zone and the detectable chemical group or the linking group of the labeled reagent.

14. The test device of claim 11 wherein the detectable chemical group in the labeled reagent possesses a physical property which is detectable in the detection zone.

15. The test device of claim 14 wherein the detectable chemical group is a fluorescer or a chromophore.

16. The test device of claim 1 wherein the detectable chemical group in the labeled reagent possesses a detectable chemical property and the detection zone is incorporated with a detectant composition which interacts with the chemical group to provide the detectable signal.

17. The test device of claim 16 wherein the detectable chemical group is (i) an enzyme or (ii) a substrate or cofactor for such enzyme, and wherein the detectant composition comprises the other thereof.

18. The test device of claim 17 wherein the substrate is chromogenic fluorogenic or chemiluminescent.

19. The test device of claim 1 wherein the reagent zone, reaction zone and detection zone are in the form of layers in fluid contact with one another.

20. The test device of claim 19 which additionally comprises a solid, nonporous support element situated on the opposite side of the detection layer from the reagent layer.

* * * * *